United States Patent [19]

Steffee

[11] Patent Number: 4,854,311

[45] Date of Patent: Aug. 8, 1989

[54] BONE SCREW

[75] Inventor: Arthur D. Steffee, Moreland Hills, Ohio

[73] Assignee: Acro Med Corporation, Cleveland, Ohio

[21] Appl. No.: 146,739

[22] Filed: Jan. 21, 1988

Related U.S. Application Data

[63] Continuation-in-part of Ser. No. 817,344, Jan. 9, 1986.

[51] Int. Cl.⁴ .............................................. A61B 17/58
[52] U.S. Cl. ............................. 128/92 YM; 128/92 Y; 128/92 YV; 411/414
[58] Field of Search ....... 128/92 YM, 92 YF, 92 VV, 128/92 Y, 92 YK, 92 YV, 69; 411/414, 411, 423, 394

[56] References Cited

U.S. PATENT DOCUMENTS

| | | | |
|---|---|---|---|
| 272,778 | 2/1883 | Schilling | 411/414 |
| 1,801,186 | 4/1931 | Arenz | 411/394 |
| 2,121,193 | 6/1938 | Hanicke | 128/92 VT |
| 2,570,465 | 10/1951 | Lundholm | 128/92 R |
| 3,489,143 | 1/1970 | Halloran | 128/92 YK |
| 3,660,233 | 5/1972 | Dalke et al. | 411/411 X |
| 3,693,616 | 9/1972 | Roaf et al. | 128/69 |
| 3,706,309 | 12/1972 | Toftness | 128/69 |
| 3,997,138 | 12/1976 | Crock et al. | 248/67.5 |
| 4,175,555 | 11/1979 | Herbert | 128/92 R |
| 4,448,191 | 5/1984 | Rodnyansky et al. | 128/69 |
| 4,456,005 | 6/1984 | Lichty | 128/92 YF X |
| 4,493,317 | 1/1985 | Klaue | 128/92 UD X |
| 4,655,199 | 4/1987 | Stefee | 128/92 YM X |

FOREIGN PATENT DOCUMENTS

| | | | |
|---|---|---|---|
| 365613 | 12/1938 | Italy | 128/92 BB |
| 1115738 | 9/1984 | U.S.S.R. | 128/92 YF |
| 13867 | 7/1893 | United Kingdom | 411/411 |

OTHER PUBLICATIONS

Journal of Bone & Joint Surgery, 1934, pp. 168–172.
Journal of Bone & Joint Surgery, vol. 18, 1936, p. 409.
American Journal of Surgery, vol. 37, #1, 1937, pp. 79–87.
Zimmer News Release, 8/1966.
Surgical Equipment, vol. 7, No. 4, 1940, pp. 14–15.
Vitallium Surgical Appliances, 1948, p. 16.

*Primary Examiner*—Robert A. Hafer
*Assistant Examiner*—Kevin G. Rooney
*Attorney, Agent, or Firm*—Tarolli, Sundheim & Covell

[57] ABSTRACT

A bone screw for use with a connecting member for connecting a bone portion with the connecting member. The bone screw includes an elongate shank having a longitudinal central axis. A first externally threaded portion receives a nut for attaching the connecting member to the bone screw. A second externally threaded portion engages a surface defining an opening in the bone portion to attach the bone screw to the bone portion. A cylindrical body portion is located on the shank intermediate the first and second externally threaded portions. The body portion engages a portion of the surface defining the opening in the bone portion to restrict movement of the bone screw relative to the bone portion in a direction transverse to the longitudinal central axis of the shank. The body portion blocks effluence from the opening in the one bone portion. A seat portion having a surface located on the body portion adjacent the first externally threaded portion engages the connecting member to establish the axial location of the connecting member along the bone screw.

16 Claims, 3 Drawing Sheets

BONE SCREW

This application is a continuation-in-part of application Ser. No. 817,344, filed Jan. 9, 1986, entitled "Bone Screw", which is assigned to the assignee of the present application.

BACKGROUND OF THE INVENTION

1. Technical Field

The present invention relates to a bone screw for use in correcting damage or deformation to a bone or group of bones in a body.

2. Description of the Prior Art

Bone screws are known in the medical profession. Typical uses for a bone screw are to treat a bone fracture, to attach a corrective device to parts of a fractured bone in the area adjacent to the fracture, or to attach a corrective device to a group of bones, such as a spinal U.S. Pat. Nos. 2,121,193 and 2,570,465 each disclose a bone screw which has a threaded portion for engaging a cancellous portion of a bone. The threaded portion has a trailing face extending in a direction which is substantially perpendicular to the longitudinal axis of the bone screw. A bone screw disclosed in U.S. Pat. No. 4,175,555 has two threads of different pitch distances for engaging bone tissue. Each of the two threads has a face, which is substantially perpendicular to the longitudinal axis of the bone screw, for applying a clamping force to fractured parts of a bone as the bone screw is advanced.

U.S. Pat. No. 3,997,138 discloses another bone screw for securing rods of a corrective device to a vertebra. The bone screw includes two threaded portions and a boss integrally formed on the bone screw. The boss is located between the two threaded portions. The boss maintains the rods spaced away from the vertebra. A washer having projections for extending into the vertebra is located between the boss and the vertebra to aid in stabilizing the bone screw in a cancellous bone.

A bone screw similar to the bone screw disclosed in U.S. Pat. No. 2,121,193, referred to above, may be used to secure a corrective device to a vertebra. A first threaded portion of the bone screw is threaded into a cancellous portion of the vertebra. A nut is threaded onto a second threaded portion of the bone screw projecting from the vertebra. A corrective device is received on the second threaded portion of the bone screw and placed against the nut. A second nut is then threaded onto the second threaded portion of the bone screw. The second nut is tightened against the corrective device to apply a clamping force to the corrective device for preventing movement of the corrective device relative to the bone screw.

Due to load being transmitted from the corrective device to the bone screw in a direction perpendicular to the longitudinal central axis of the bone screw, the bone screw tends to move relative to the vertebra or the second threaded portion tends to bend relative to the first threaded portion. This bending of the bone screw could result in a crack developing in the surface of the bone screw and eventual failure. Also, if the corrective device is not seated properly between the nuts, a localized bending stress concentrates in the bone screw adjacent the nuts and the bone screw may break.

Furthermore, some fluids of the body are corrosive. If the surface of the bone screw pits due to the corrosive action of the fluids in an area of relatively high stress, cracks may initiate and eventual failure of the bone screw could occur. These fluids often flow to the highly stressed area of the bone screw from an opening in the vertebra for the bone screw.

SUMMARY OF THE INVENTION

The present invention provides a bone screw having a thread configuration which provides solid mounting for the bone screw in a cancellous bone. A crest portion of the thread is impaled in the cancellous bone to increase the resistance to removal of the bone screw from the bone. In addition, the bone screw has increased strength in areas which are normally subjected to the highest stress and which are prone to breakage. The bone screw has a reference surface which aids the surgeon in determining when the bone screw has been advanced into the bone a desired distance.

The bone screw has a combination retaining and seal section. The retaining and seal section has a relatively large area of engagement with an opening formed in the bone to restrict movement of the bone screw relative to the bone in a direction perpendicular to the longitudinal central axis of the bone screw. The retaining and seal section also tends to minimize bending of the bone screw. In addition, the large area of engagement between the bone and the retaining and seal section enables the bone screw to block the flow of fluid from an opening formed in the bone for the bone screw.

In one embodiment of the bone screw, a standard external thread convolution is formed on one end portion of the bone screw to receive a nut to attach the bone screw to a corrective device. A coarse external thread convolution is formed on the opposite end of the bone screw to engage a cancellous bone. The coarse thread convolution has leading and trailing faces. The leading face is angled rearwardly approximately 45 degrees relative to the longitudinal axis of the bone screw. The trailing face is angled rearwardly approximately 80 degrees relative to the longitudinal axis of the bone screw to intersect the leading face of the same thread convolution and form a crest. The leading and trailing faces of adjacent thread convolutions intersect in an arcuate root portion having a radius of curvature. The crest is offset rearwardly of the forward most portion of the trailing face by a distance less than the radius of curvature of the arcuate root portion to form a recess for a portion of the cancellous bone to project into to form a solid mounting for the bone screw in the bone.

Once the coarse thread convolution of the bone screw is advanced a desired distance into the bone, a connecting member of a corrective device is received on the bone screw and a nut is threaded onto the standard thread convolution. As the nut is tightened against the connecting member, a tensile force is imparted through the bone screw, and the crests of the coarse thread convolution are impaled in the cancellous bone as the bone screw is urged to move in a direction towards the nut.

In another embodiment of the bone screw, the bone screw is used to attach a connecting member of a corrective device to a cancellous bone. The bone screw includes an elongate shank having a longitudinal central axis. A first externally threaded portion is used for attaching the connecting member to the bone screw. A second externally threaded portion is for threaded engagement with a surface defining an opening in bone to attach the bone screw to the bone.

A cylindrical body portion on the shank is located between the first and second externally threaded portions. The body portion has a diameter substantially equal to the crest diameter of the threads on the second externally threaded portion. The length of the body portion is less than the pitch of the second externally threaded portion. The body portion engages a portion of the surface defining the opening in the bone to restrict movement of the bone screw relative to the bone in a direction transverse to the longitudinal central axis of the shank. The body portion also blocks fluid flow from the opening in the bone.

The thread convolution of the second externally threaded portion located adjacent the body portion has a root with a radius greater than the radius of the root of the other thread convolutions of the second externally threaded portion. A seat portion is located on the body portion adjacent the first externally threaded portion. The seat portion has a surface for engaging the connecting member to establish the axial location of the connecting member along the bone screw.

A shoulder portion is located between the seat portion and the body portion. The shoulder portion has a tapering circular surface with a diameter which increases as the shoulder portion extends in a direction from the body portion toward the seat portion. A second shoulder portion is located between the seat portion and the first externally threaded portion. The second shoulder portion has a tapering circular surface which increases in diameter as the second shoulder portion extends in a direction from the first threaded portion toward the seat portion.

BRIEF DESCRIPTION OF THE DRAWINGS

Further features of the present invention will become apparent to those skilled in the art to which the present invention relates from reading the following specification with reference to the accompanying drawings, in which.

DETAILED DESCRIPTION OF PREFERRED EMBODIMENTS

Figure 1:
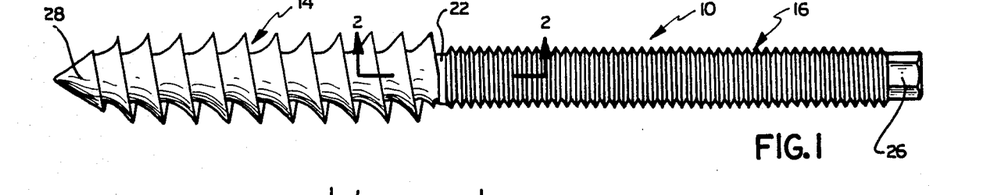
FIG. 1 is an enlarged elevational view illustrating a bone screw made in accordance with one embodiment of the present invention.

The bone screw 10, illustrated in FIG. 1, connects a corrective device to a bone or connects fractured parts of the same bone together. The bone screw 10 has a mounting section or coarse threaded portion 14 and a connector section or standard threaded portion 16 coaxially arranged along a shank 22. The shank 22 has an elongate cylindrical shape. The bone screw 10 is made from a material that is compatible with human bone tissue. Preferably, such a material is a titanium based alloy or a surgical grade stainless steel.

Figure 3:
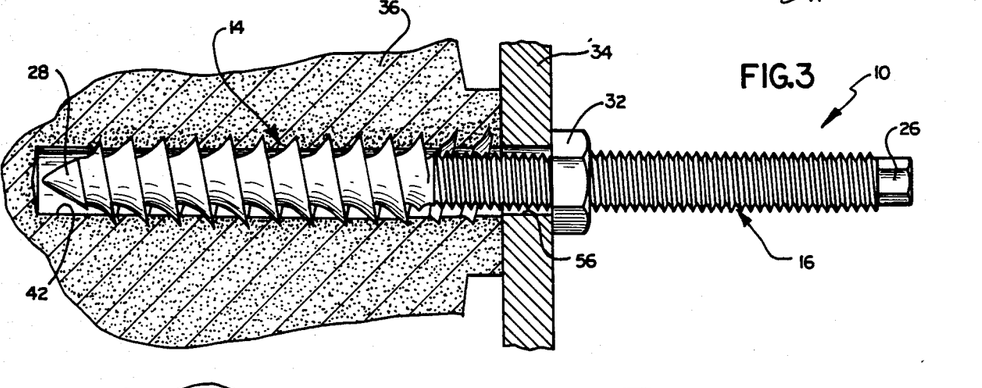
FIG. 3 is an enlarged schematic view, partially in section, illustrating the bone screw in FIG. 1 connecting a corrective device to a bone.

The coarse threaded portion 14 has an external mounting thread convolution for engaging a cancellous bone. The standard threaded portion 16 receives a connecting member of a corrective device, such as a spine plate 34, and a standard nut 32 (FIG. 3). The nut 32 is tightened on the bone screw 10 to clamp the spine plate 34 to a vertebra 36.

The bone screw 10 also has a driving end portion 26 and a tapered end portion 28 located at axially opposite ends. The driving end portion 26 is used for rotating the bone screw 10 to advance the bone screw into the vertebra 36. The driving end portion 26 has an external hex head configuration, but other configurations could be adapted equally well. For example, a hex socket or a standard slotted screw head could be used. The tapered end portion 28 aligns the bone screw 10 in an opening 42 in the vertebra 36. The tapered end portion 28 also allows crests of the coarse threads 14 on the tapered portion to gradually engage the surface defining the opening 42 and advance the bone screw 10 upon rotation of the bone screw.

Figure 2:
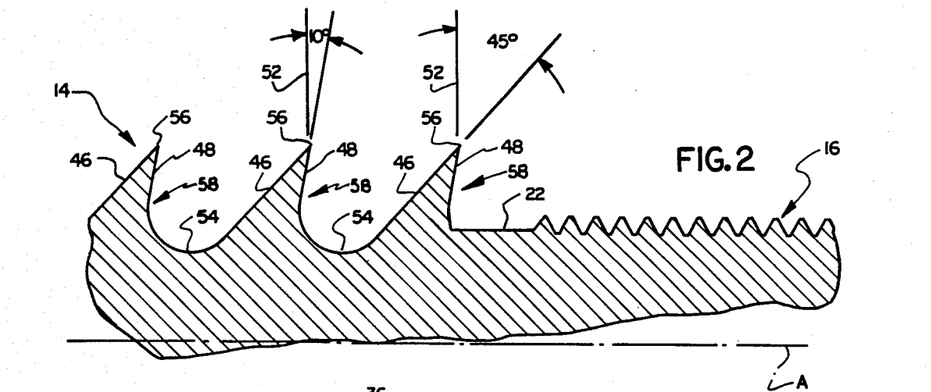
FIG. 2 is an enlarged cross sectional fragmentary view taken approximately along line 2—2 of FIG. 1.

The coarse threaded portion 14 and standard threaded portion 16 each have one thread spirally arranged on the exterior of the shank 22. The shank 22 has a longitudinal central axis A. The configuration of the coarse threaded portion 14 is illustrated in detail in FIGS. 2 and 6. The coarse threaded portion 14 has a leading face 46 and a trailing face 48 relative to the direction the bone screw 10 advances into the vertebra 36, to the left as viewed in FIGS. 2 and 6. The leading face 46 faces forward in a direction away from the standard threaded portion 16 and is angled to the rear of the bone screw 10 between 40° and 50°. Preferably, the leading face 46 is disposed at a 45° angle relative to a line 52 normal to the longitudinal central axis A, or 45 degrees relative to the longitudinal central axis. The trailing face 48 faces toward the standard threaded portion 16 and is angled to the rear of the bone screw 10 between 5° and 15°. Preferably, the trailing face 48 is disposed at a 10° angle relative to the line 52 normal to the longitudinal central axis A, or 80 degrees relative to the longitudinal central axis.

An arcuate root portion 54 having a radius R (FIG. 6) is formed between the faces 46, 48 of adjacent thread convolutions. The leading face 46 and trailing face 48 of the same thread convolution intersect to form a crest 56. The trailing face 48 slopes rearwardly and radially outwardly from the arcuate root portion 54 to the crest 56. The crest 56 is offset rearwardly from the forwardmost portion 48a of the trailing face 48 by a distance Q which is less than the radius R of curvature of the arcuate root portion 54 to form a rearwardly facing recess 58.

The recess 58 is formed between the crest 56 and the arcuate root portion 54. A portion of the cancellous bone extends into the recess 58 and is trapped by the recess. If a force attempts to move the bone screw 10 axially to the right, as viewed in FIG. 6, the crests 56 are impaled in the cancellous bone and the portion of the cancellous bone trapped in the recess 58 must be forced rearwardly and radially outwardly of the recess before the bone screw may move to the right.

Figure 6:
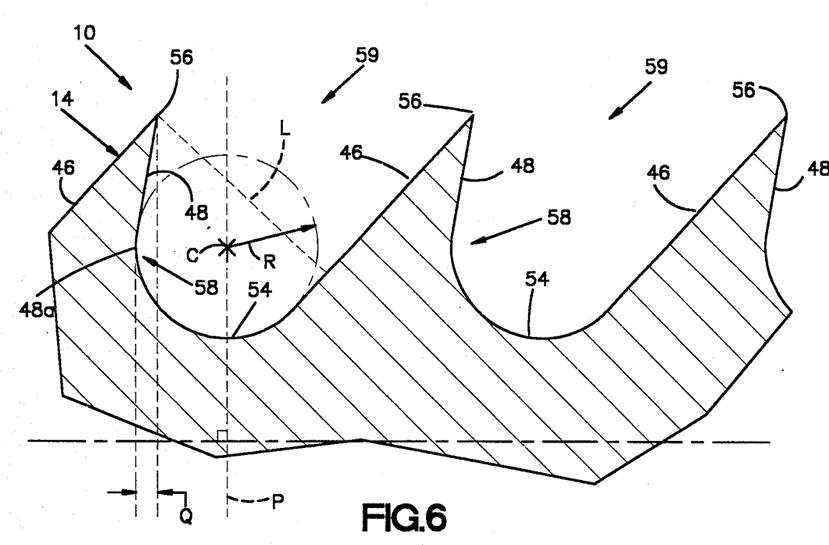
FIG. 6 is an enlarged cross sectional fragmentary view of a portion of the bone screw in FIG. 2.

A relatively wide opening 59 is formed between the crests 56 of adjacent thread convolutions of the coarse threaded portion 14. A portion of the cancellous bone in which the bone screw 10 is used projects into the relatively wide opening 59 between crests 56 of adjacent threads on opposite sides of a radial plane P. The plane P extends through a center of curvature C of the arcuate root portion 54 and perpendicular to the longitudinal central axis A of the bone screw 10 and does not intersect any portion of a thread convolution of the coarse threaded portion 14. The thread configuration of the threaded portion 14 allows a relatively thick portion of the cancellous bone to extend into the relatively wide opening 59 between the adjacent crests 56. Thus, a relatively strong portion of the cancellous bone forms a solid mounting for the bone screw 10 in the bone.

A line L extending perpendicular to the leading face 46 of one of the thread convolutions of the coarse threaded portion 14 and extending through the crest 56 of the next forward adjacent thread convolution is disposed radially outwardly from the center of curvature C of an arcuate root portion 54. The distance that the line L extends radially outwardly of the center of curvature C of the arcuate root portion 54 is less than the radius R of the arcuate root portion. Thus, a cross section of any of the thread convolutions of the coarse threaded portion 14, taken in a radial plane containing the longitudinal central axis A is relatively thick and, therefore, relatively strong and relatively more resistant to breakage than heretofore known screws with rearwardly angled trailing faces.

In one embodiment, the coarse threaded portion 14 has a crest diameter of approximately 0.25 inch and a pitch of 10 threads per inch extending for approximately 1¼ inches along the shank 22. The standard thread portion 16 is a 10-32 NF-2 thread of 3/16 inch diameter extending for approximately 1½ inches along the shank 22. The drive portion 26 has a hexagonal head configuration for gripping with a suitable tool (not shown). The width across the corners of the driving portion 26 is slightly smaller than the root diameter of the standard thread portion 16 to allow the nut 32 pass over the driving portion.

To install the bone screw 10 in the vertebra 36 (FIG. 3), an opening 42 is formed in the vertebra 36. The opening 42 will have a diameter which is at least as large as the shank 22. The opening 42 will extend slightly deeper into the vertebra 36 than the depth that the coarse threaded portion 14 will extend. The opening 42 is then tapped with a tap having a thread profile which is approximately the same as the thread configuration of the coarse threaded portion 14. It has been found that the bone screw 10 requires a larger axial force to remove it from the vertebra 36 if the opening 42 is tapped before the bone screw is threaded into the opening than if the opening is not tapped. The bone screw 10 is then placed in the opening 42 and gripped with a suitable tool at the driving portion 26. The tool is rotated about the longitudinal central axis A of the bone screw 10 so the bone screw advances (to the left as viewed in FIG. 3) relative to the vertebra 36. The bone screw 10 is rotated until the bone screw extends a desired distance into the vertebra 36, then the tool is removed.

The spine plate 34 is connected to the vertebra 36 by placing the spine plate on the bone screw 10 so the standard thread portion 16 of the bone screw 10 extends through an opening 56 in the spine plate. The nut 32 is then threaded onto the standard thread portion 16 and tightened against the spine plate 34 to firmly clamp the spine plate against the vertebra 36. Tightening the nut 32 against the spine plate 34 also applies a tensile force to the bone screw 10 attempting to pull the bone screw axially to the right, as viewed in FIG. 3. However, the coarse threaded portion 14 engaging the vertebra 36 prevents removal of the bone screw 10. When the desired tightness of the nut 32 has been achieved, the standard thread portion 16 of bone screw 10 is then trimmed off adjacent to the nut 32.

Under normal circumstances and loads, tightening of the nut 32 does nothing more than further impale the crests 56 of the coarse thread portion 14 rearwardly into the cancellous bone tissue. If the trailing face 48 was perpendicular to the longitudinal axis of the bone screw 10, or forwardly angled, the trailing face would not hold the bone screw as securely in the cancellous bone as the rearwardly disposed trailing face of the thread configuration according to the present invention because the cancellous bone could be more easily pushed radially outward along the trailing face.

Furthermore, tightening the nut 32 draws together and clamps the spine plate 34 against the vertebra 36. Since the bone screw 10 is not rotated to accomplish the clamping action, the vertebra and the spine plate 34 are not rotated relative to one another. This allows movement and a clamping force only along a direction parallel to the longitudinal central axis A of the bone screw 10.

Figure 4:
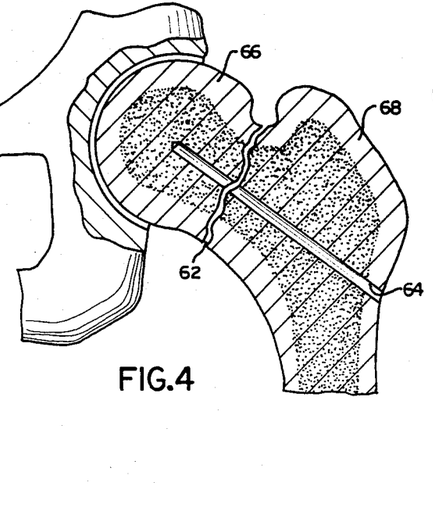
FIG. 4 is a schematic view, partially in section, illustrating a fractured femur before a bone screw is installed.
Figure 5:
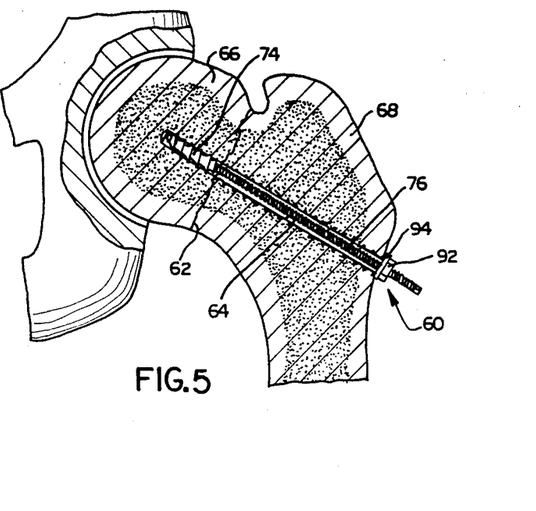
FIG. 5 is a schematic view similar to FIG. 4 illustrating a bone screw and nut installed.

In another embodiment of the present invention, a bone screw 60 is used to reduce a bone fracture. FIG. 5 illustrates the bone screw 60 reducing a fracture 62 of the femoral neck. This is accomplished by first drilling an opening 64 (FIG. 4) completely through the upper portion 68 of the femur and partially through the ball portion 66. It will be obvious to one skilled in the art that the opening 64 must be drilled coaxially in the two fractured parts so that when the fracture 62 is reduced, the fractured surfaces will mate to assure proper healing.

The bone screw 60 is then rotated as described above to advance the coarse threaded portion 74 to the position illustrated in FIG. 5. The coarse threaded portion 74 has a thread configuration similar to that described above. However, the coarse threaded portion 74 extends for a length of about ½ to ¾ of an inch along the shank. This assures that the coarse threaded portion 74 engages only the ball portion 66 side of the fracture 62. The standard thread portion 76 extends for about two inches through opening 64. A nut 92 and washer 94 are received on the standard thread portion 76. The nut 92 is tightened so that the washer 94 engages the upper portion 68 of the femur in order to move and clamp the fractured parts 66, 68 together. Again, neither the ball portion 66 nor the upper portion 68 is subject to rotational forces, so that the fractured surfaces are drawn together along a direction parallel to the axis of the bone screw 60 in order to properly mate. Once the fracture is reduced to the desired position, the standard thread portion 76 which extends beyond the nut 92 is trimmed adjacent to the nut.

Figure 7:
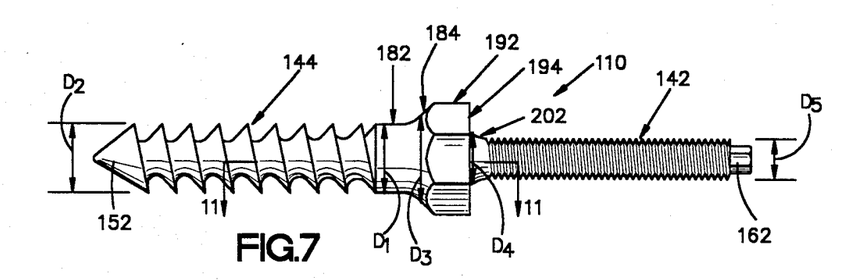
FIG. 7 is an enlarged elevational view illustrating a bone screw according to another embodiment of the present invention.

Another embodiment of a bone screw 110 according to the present invention is illustrated in FIG. 7. The bone screw 110 is for use with a connecting member 120 (FIG. 9) of a corrective device for connecting bone portions together. The bone screw 110 is threaded into a bone portion 122 to connect the connecting member 120 with the bone portion. The bone portions may be parts of a fractured bone or may be different bones of a group of bones, such as vertebrae of a spinal column.

The bone screw 110 is made from a material compatible with human tissue, such as surgical grade stainless steel or titanium. The bone screw 110 includes an elongate cylindrical shank 132 (FIG. 11) having a longitudinal central axis B. The bone screw 110 has an externally threaded portion 142 integrally formed on the shank 132 and extending longitudinally along a portion of the shank. The threaded portion 142 of the bone screw 110 is identical to the standard threaded portion 16 of the bone screw 10, described above. The threaded portion 142 receives a standard internally threaded nut 146 (FIG. 9) to secure the connecting member 120 to the bone screw 110.

Figure 8:
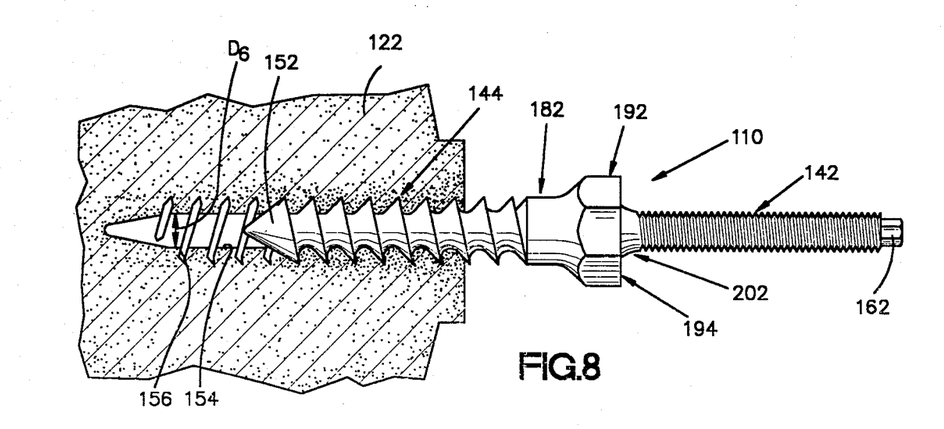
FIG. 8 is an enlarged view, partly in section, illustrating the bone screw in FIG. 7 partially threaded into a vertebra.
Figure 9:
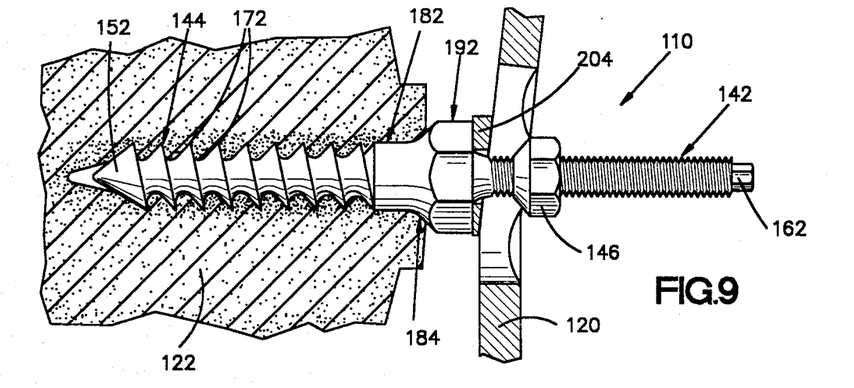
FIG. 9 is a view, similar to FIG. 8, illustrating the bone screw attaching a connecting member of a corrective device to a vertebra.
Figure 10:
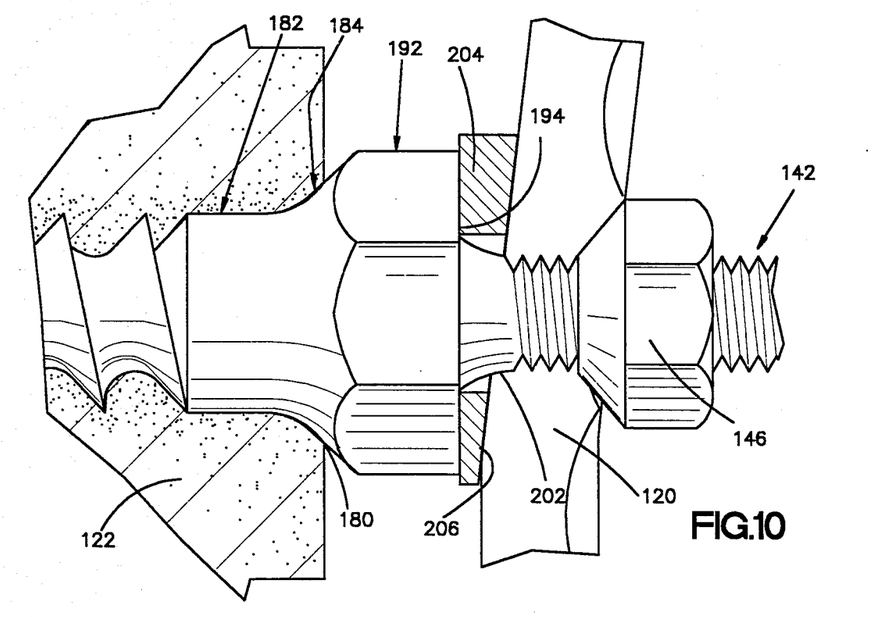
FIG. 10 is an enlarged view of a portion of FIG. 9.

The bone screw 110 also has another externally threaded portion 144 integrally formed on the shank 132 and extending longitudinally along another portion of the shank. The threaded portion 144 of the bone screw 110 is identical to the coarse threaded portion 14 of the bone screw 10 (FIG. 1), described above. The threaded portion 144 is for connecting the bone screw 110 to a cancellous bone portion 122, such as a vertebra, as illustrated in FIGS. 8–10.

The thread of the threaded portion 144 has a crest diameter $D_2$ (FIG. 7) which is larger than the crest diameter $D_5$ of the thread of the threaded portion 142. The threaded portion 144 has a tapered end portion 152 which pilots the bone screw 110 in an opening 154 (FIG. 9) formed in the bone portion 122. The opening 154 is defined by a surface having a diameter $D_6$ (FIG. 8) and preferably has a thread 156 tapped in the opening prior to threading the bone screw 110 into the bone portion 122. The tapped thread 156 preferably has the same configuration as the threaded portion 144 of the bone screw 110. The crest diameter $D_2$ of the threaded portion 144 preferably at least as large as the diameter $D_6$ (FIG. 8) of the opening 154.

Figure 11:
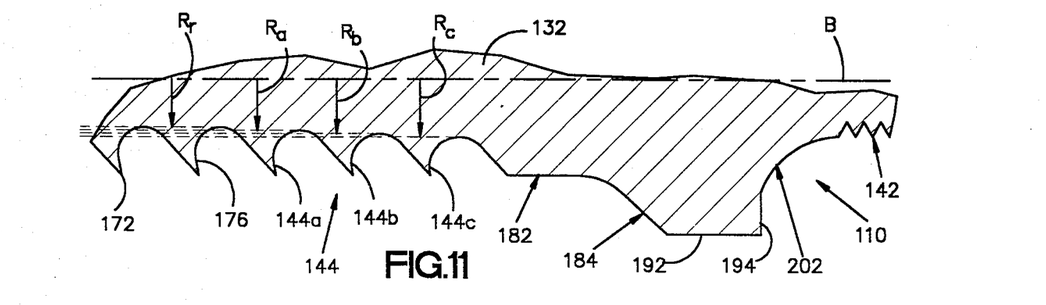
FIG. 11 is an enlarged cross sectional fragmentary view of the bone screw in FIG. 7, taken approximately along line 11—11 in FIG. 7.

The last three thread convolutions 144a, 144b, 144c (FIG. 10) of the threaded portion 144 are formed so the radii Ra, Rb, Rc, respectively, of the root of each thread convolution increases as the thread progresses toward the right, as illustrated in FIG. 11. The root radii Ra, Rb, Rc of the last three thread convolutions 144a, 144b 144c are greater than the root radius Rr of the other threads on the threaded portion 144. The radii Ra, Rb, Rc of the roots of the thread convolutions 144a, 144b, 144c preferably increase along a line disposed at an angle relative to the longitudinal central axis B of at least 1°. The increased radii Ra, Rb, Rc provides the bone screw 110 with additional strength in the area of the last three thread convolutions 144a, 144b, 144c. Thus, if any forces are transmitted through the bone screw 110 from the connecting member 120 tending to bend the bone screw in the area of the last three thread convolutions 144a, 144b, 144c, the force acts on a cross-sectional area, taken in a plane perpendicular to the longitudinal central axis B, which is larger than the cross-sectional area of the bone screw taken through a portion of a thread convolution having a root radius Rr.

The bone screw 110 also has a drive portion 162 (FIG. 9) for engagement with a suitable tool (not shown), such as a wrench. The drive portion 162 is located at an axial end portion of the bone screw 110 adjacent the first threaded portion 142. When a force is applied through the tool to the drive portion 162 to rotate the bone screw 110 about its longitudinal central axis B (FIG. 11), the threaded portion 144 advances or threads into the tapped thread 156 in the opening 154 (FIG. 8) in the bone portion 122. As described above, the interaction of the crests 172 and trailing face 176 of the threaded portion 144 with the cancellous tissue of the bone portion 122 prevents the bone screw 110 from being removed from the bone portion by forces acting to move the bone screw axially to the right, as viewed in FIG. 9, relative to the bone portion.

The bone screw 110 includes a cylindrical body portion 182 (FIG. 7) located between the threaded portions 142, 144. The cylindrical body portion 182 is defined by a surface having a diameter $D_1$ which is substantially equal to the crest diameter $D_2$ of the threaded portion 144 and, thus, is larger than the diameter $D_6$ (FIG. 8) of the opening 154. The axial extent Y (FIG. 8) or length of the body portion 182 is preferably less than the pitch X of the threaded portion 144. When the bone screw 110 is advanced into the bone portion 122, from the position illustrated in FIG. 8 to the position illustrated in FIG. 9, the body portion 182 engages a portion of the bone portion 122 surrounding the opening 154.

As the bone screw 110 advances in the opening 154 to the position illustrated in FIG. 9, the body portion 182 forces a portion of the cancellous bone tissue of the bone portion 122 adjacent the tapped thread 156 forward and radially outward into the tapped thread so no radial clearance exists between the body portion and the surface of the opening. The axial extent Y of the body portion 182 is shorter than the pitch X of the threaded portion 144, and thus is shorter than the pitch of the tapped thread 156, to assure that a minimum amount of deformation of the bone portion 122 occurs adjacent the opening 154. If too much deformation of the bone portion 122 is caused by the bone screw 110, damage to the bone portion could result.

The body portion 182, thus, is in circumferential engagement with the surface defining the opening 154 in the bone portion 122. The body portion 182 restricts the bone screw 110 from moving relative to the bone portion 122 in a direction transversely to the longitudinal central axis B of the bone screw. The body portion 182 also seals or restricts the flow of body fluids from the opening 154 to the areas of the bone screw outside the bone portion 122 which are normally subjected to the highest stress.

An alternate drive portion 192 having a hex head configuration is formed on the shank 132 between the threaded portion 142 and the body portion 182. The drive portion 192 is engageable by a suitable tool to prevent the rotation of the bone screw 110 during tightening of the nut 146 on the threaded portion 142. The drive portion 192 may also be used to remove the bone screw 110 after the connecting member 120 is removed from a patient, as is typically done in the case of a relatively young patient who has recovered from the injury or damage that the connecting member was used to correct.

A shoulder portion 184 (FIG. 7) is disposed adjacent the body portion 182 between the alternate drive portion 192 and the body portion 182. The shoulder portion 184 acts to eliminate any stress risers which could result from a stepped transition between the body portion 182 and the alternate drive portion 192. The shoulder portion 184 is defined by a circular and axially tapered surface. The tapered surface of the shoulder portion 184 has a diameter $D_3$ which increases as the tapered surface extends in a direction from the body portion 182 toward the alternate drive portion 192. The diameter $D_3$ of the tapered surface of the shoulder portion 184 is greater than the diameter $D_2$ of the body portion 182.

As the bone screw 110 is advanced into the opening 154 in the bone portion 122, the tapered surface of the shoulder portion 184 engages the circumferential edge 180 at the end of the opening 154 to further aid in preventing movement or "wobble" of the bone screw relative to the bone portion. Since the body portion 182 engages a circumferential portion of a portion of the surface defining the opening 154 and the shoulder portion 184 engages the circumferential edge 180 of the opening 154, a seal is created between the part of the bone screw 110 extending from the opening 154 and the bone portion 122. The sealing action of the body portion 182 and shoulder portion 184 restricts the flow of body fluids from the opening 154 in the bone portion 122. Thus, the flow of corrosive body fluids from the opening 154 in the bone portion 122 is further blocked to prevent corrosion to the bone screw 110 in the areas of highest stress, which are typically located between the threaded portions 142, 144.

The shoulder portion 184 also provides a bone screw 110 with a relatively shorter moment arm between its rightmost engagement point with the edge 180 of the bone portion 122, as viewed in FIG. 9, and the connecting member 120 than if no shoulder portion was present. If no shoulder portion was present, the rightmost engagement point of the bone screw and bone portion, about which the bone screw tends to bend, would be inside the bone portion. The relatively shorter moment arm reduces the torque (from the equation torque = force X moment arm) and, thus, the stress in the bone screw 110 resulting from the force transmitted from the connecting member 120 tending to bend the bone screw about the edge 180 of the bone portion 122.

A relatively strong bone screw 110 is provided since the shoulder portion 184 has a relatively large cross-section, taken perpendicularly to the longitudinal central axis B at the engagement point 180, to distribute the force over a relatively large area tending to bend the bone screw about the edge 180. The shoulder portion 184 also forms a reference surface integrally formed on the bone screw 110. The reference surface enables the surgeon to know how far the threaded portion 144 extends into the bone portion 122 since the length that the threaded portion extends from the shoulder portion 184 is known before threading the bone screw 110 into the bone portion.

A seat portion 194 has a planar surface integrally formed at an axial end of the alternate drive portion 192 adjacent the threaded portion 142. The seat portion 194 engages the connecting member 120 to establish the axial location of the connecting member along the bone screw 110 and to space the connecting member from the bone portion 122. Forming the seat portion 194 integrally on the bone screw 110 assures that the surface engaged by the connecting member 120 will not loosen and move relative to the bone screw after the surgical procedure so the location of the connecting member 120 along the bone screw does not change.

Another shoulder portion 202 extends between the seat portion 194 and the threaded portion 142. The shoulder portion 202 eliminates any stress risers which could result from a stepped transition between the seat portion 194 and the threaded portion 142. The shoulder portion 202 is defined by a circular and axially tapered surface. The tapered surface of the shoulder portion 202 has a diameter $D_4$ that increases as the shoulder portion extends from the threaded portion 142 to the seat portion 194. The diameter $D_4$ of the tapered surface defining the shoulder portion 202 is greater than the crest diameter $D_5$ of the threaded portion 142. The increasing diameter $D_4$ of the shoulder portion 202, thus, provides a relatively large cross-sectional area, taken perpendicular to the longitudinal central axis B, over which to distribute the forces to reduce the stress and provide a bone screw 110 less prone to failure.

If the connecting member 120 is bent to conform to a desired curvature, as illustrated in FIGS. 9 and 10, a space may result between the seat portion 194 and the connecting member. If the nut 146 is tightened against the connecting member 120, stress may concentrate in the portion of the bone screw 110 adjacent the seat portion 194 by the threaded portion 142 attempting to bend or pivot relative the threaded portion 144. To avoid this relative bending, a washer 204 having an angled or wedge-shaped configuration is preferably used between the seat portion 194 and the connecting member 120. The configuration or angle of the washer 204 is chosen to closely match the angle of the space between the connecting member 120 and the seat portion 194. The connecting member 120 will contact the entire angled surface 206 of the washer 204 and evenly distribute load over the surface area of the seat portion 194 so the threaded portion 142 does not tend to bend relative to the threaded portion 144.

From the above description of a preferred embodiment of the invention, those skilled in the art will perceive improvements, changes and modifications. Such improvements, changes and modifications within the skill of the art are intended to be covered by the appended claims.

Having described a specific preferred embodiment of the invention, the following is claimed:

1. A bone screw for use in connecting a bone portion with a connecting member, said bone screw comprising:
a mounting section disposed at a first end portion of said bone screw for engaging the bone portion; and
a connector section disposed at a second end portion of said bone screw for use in connecting said bone screw with the connecting member;
said mounting section including an external mounting thread convolution having a root portion, a crest portion, a leading flank surface extending between said root and crest portions and facing forwardly in a direction away from said connector section, and a trailing flank surface extending between said crest and root portions and facing rearwardly in a direction towards said connector section, said root portion having an arcuate cross sectional configuration in a radial plane containing the longitudinal central axis of said bone screw, said trailing flank surface sloping rearwardly and outwardly from said root portion to said crest portion, said crest portion of said mounting thread convolution being offset rearwardly of the forwardmost portion of said trailing flank surface by a distance which is less than the radius of curvature of the arcuate root portion of said mounting thread convolution to form a rearwardly facing recess between said crest and root portions of said mounting thread convolution and to form a wide space between adjacent turns of said crest portion of said mounting thread convolution through which bone may project radially inwardly into the space between adjacent turns of said mounting thread convolution on opposite sides of a radial plane extending through the center of curvature of said root portion and perpendicular to the longitudinal central axis of said bone screw to form a solid mounting for said bone screw in the bone.

2. A bone screw as set forth in claim 1 wherein a line extending perpendicular to the leading flank of one turn of the thread convolution and extending through the crest of the next forward turn of the thread convolution is disposed radially outwardly from the center of curvature of the arcuate root portion of the thread convolution by a distance which is less than the radius of curvature of the arcuate root of the thread convolution.

3. The bone screw set forth in claim 1 wherein said leading flank surface extends at an angle of between 40° and 50° relative to the longitudinal central axis of said bone screw and said trailing flank surface extends at an angle of between 75° and 85° relative to the longitudinal central axis of said bone screw.

4. The bone screw set forth in claim 1 further including means for engaging a portion of a surface defining an opening in the bone portion to restrict movement of said bone screw relative to the bone portion in a direction transverse to the longitudinal central axis of said bone screw and to block effluence from the opening in the bone portion, said means being located intermediate said connector section and said mounting section.

5. A bone screw for connecting a bone portion with a bone connecting member, said bone screw comprising:
an elongated shank having a longitudinal central axis, a first externally threaded portion for receiving an internally threaded nut and a second externally threaded portion for threaded engagement with a surface defining an opening in the bone portion to attach the bone screw to the bone portion; and
means integral with said shank and having a transverse cross-section at least equal to the transverse cross-section of the opening in the bone portion for projecting into the opening and for engaging a portion of the surface defining the opening in the bone portion to restrict movement of said bone screw relative to the bone portion in a direction transverse to the longitudinal central axis of said shank and to block effluence from the opening in the bone portion, said means being located intermediate said first externally threaded portion and said second externally threaded portion.

6. The bone screw set forth in claim 5 wherein said means includes a longitudinally extending cylindrical body portion having a diameter substantially equal to the crest diameter of the thread on said second externally threaded portion and a shoulder portion located between said first externally threaded portion and said body portion, said shoulder portion having a circular tapering surface with a diameter which increases as said shoulder portion extends from said body portion toward said first externally threaded portion, the diameter of the circular tapering surface defining said shoulder portion being greater than the diameter defining said body portion, said body portion having a longitudinal extent which is less than the pitch of the thread of said second externally threaded portion.

7. The bone screw set forth in claim 6 wherein said second externally threaded portion includes a thread having a leading face and a trailing face, said leading face being disposed at a first acute angle relative to the longitudinal central axis of said shank, said trailing face being disposed at a second acute angle relative to the longitudinal central axis of said shank in the same direction as said leading face, said trailing face intersecting said leading face on the same thread turn forming the crest radially outwardly of said shank, said trailing face intersecting said leading face of an adjacent thread turn forming an arcuate root portion in a radial plane containing the longitudinal central axis of said bone screw, said arcuate root portion having a radius of curvature, said trailing face sloping rearwardly so said crest is offset from the forwardmost portion of the trailing face by a distance which is less than the radius of curvature of said root portion to form a recess between the crest and root portion for a portion of the bone portion to project into and form a solid mounting for said bone screw in the bone portion.

8. The bone screw set forth in claim 6 further including a first driving portion for transmitting a force to said shank to rotate said shank about its longitudinal central axis for threading said second externally threaded portion in the opening in the bone portion upon the application of the force to said driving portion, said first driving portion being disposed at an axial end portion of said bone screw which is trimmed away after said second externally threaded portion is threaded into the opening in the bone portion, a second driving portion located between said first and second externally threaded portions for rotating said shank about its longitudinal central axis to remove said second externally threaded portion from the bone portion after the first driving portion has been trimmed away.

9. The bone screw set forth in claim 6 wherein said second externally threaded portion further includes at least one thread located adjacent said body portion having a root diameter greater than the root diameter of other threads on said second externally threaded portion.

10. An apparatus comprising:
a bone connecting member to be connected with a bone portion; and
a bone screw for connecting the bone connecting member with the bone portion, said bone screw comprising:
an elongated shank having a longitudinal central axis, a first externally threaded portion for receiving an internally threaded nut and a second externally threaded portion for threaded engagement with a surface defining an opening in the bone portion to attach the bone screw to the bone portion; and
means integral with said shank and located intermediate said bone connecting member and said second externally threaded portion for projecting into the opening in the bone portion, said means having a transverse cross-section at least equal to the transverse cross-section of the opening in the bone portion for engaging a portion of the surface defining the opening in the bone portion to restrict movement of said bone screw relative to the bone portion in a direction transverse to the longitudinal central axis of said shank and to block effluence from the opening in the bone portion.

11. The bone screw set forth in claim 10 wherein said means on said shank includes a longitudinally extending cylindrical body portion having a diameter substantially equal to the crest diameter of the thread on said second externally threaded portion and a shoulder portion located between said second externally threaded portion and said body portion, said shoulder portion having a circular tapering surface which increases in diameter as said shoulder portion extends from said body portion toward said first externally threaded portion, the diameter of the circular tapering surface defining said shoulder portion being greater than the diameter of said body portion, said body portion having a longitudinal extent which is less than the pitch of the thread of said second externally threaded portion.

12. The bone screw set forth in claim 10 wherein said second externally threaded portion further includes at least one thread located adjacent said body portion having a root diameter greater than the root diameter of other threads on said second externally threaded portion.

13. The bone screw set forth in claim 10 wherein said second externally threaded portion has a thread with a crest diameter greater than the crest diameter of a thread on said first externally threaded portion.

14. An apparatus as set forth in claim 10 wherein said bone screw comprises a seat portion on said shank having a surface for engaging said bone connecting member to establish the axial location of said bone connecting member along said bone screw.

15. A bone screw for use with a connecting member to connect a bone portion with the connecting member, said bone screw comprising:

an elongate shank having a longitudinal central axis, a first externally threaded portion for receiving an internally threaded nut to attach the connecting member to said bone screw and a second externally threaded portion for threaded engagement with a surface defining an opening in the bone portion to attach said bone screw to the bone portion;

means integral with said shank for engaging a portion of the surface defining the opening in the bone portion to restrict movement of said bone screw relative to the bone portion in a direction transverse to the longitudinal central axis of said shank and to block effluence from the opening in the bone portion, said engaging means being located intermediate said first externally threaded portion and said second externally threaded portion, said engaging means including a longitudinally extending cylindrical body portion having a diameter substantially equal to the crest diameter of the thread on said second externally threaded portion and a first shoulder portion located between said first externally threaded portion and said body portion, said first shoulder portion having a circular tapering surface with a diameter that increases as said first shoulder portion extends from said body portion toward said first externally threaded portion, the diameter of the circular tapering surface defining said first shoulder portion being greater than the diameter defining said body portion; and a second shoulder portion located intermediate said body portion and said first externally threaded portion and having a circular tapering surface which increases in diameter as said second shoulder portion extends from said first threaded portion toward said body portion, the diameter of the circular tapering surface defining said second shoulder portion being greater than the root diameter of the thread on said first threaded portion.

16. A bone screw for use with a connecting member for connecting a bone portion with the connecting member, said bone screw comprising:

an elongate shank having a longitudinal central axis, a first externally threaded portion for receiving an internally threaded nut to attach the connecting member to said bone screw and a second externally threaded portion for threaded engagement with a surface defining an opening in the bone portion to attach said bone screw to the bone portion;

means on said shank and located intermediate said first externally threaded portion and said second externally threaded portion for engaging a portion of the surface defining the opening in the bone portion to restrict movement of said bone screw relative to the bone portion in a direction transverse to the longitudinal central axis of said shank and for blocking effluence from the opening in the bone portion;

a seat portion located on said body portion adjacent said first threaded portion having a surface for engaging the connecting member to establish the axial location of the connecting member along said bone screw; and a shoulder portion located intermediate said seat portion and said first externally threaded portion and having a circular tapering surface which increases in diameter as said shoulder portion extends from said first threaded portion toward said seat portion, the diameter of the circular tapering surface defining said shoulder portion being greater than the root diameter of the thread on said first threaded portion.

* * * * *